United States Patent [19]

Spencer

[11] 4,451,566
[45] May 29, 1984

[54] METHODS AND APPARATUS FOR ENZYMATICALLY PRODUCING ETHANOL

[76] Inventor: Donald B. Spencer, 2813 Wall St., Waukegan, Ill. 60085

[21] Appl. No.: 327,349

[22] Filed: Dec. 4, 1981

[51] Int. Cl.³ .............................................. C12P 7/14
[52] U.S. Cl. .................................. 435/162; 435/175; 435/288; 435/813; 435/814; 435/815; 435/819
[58] Field of Search ............... 435/161, 162, 163, 165, 435/175, 288, 813, 814, 815, 819

[56] References Cited

U.S. PATENT DOCUMENTS

| | | | |
|---|---|---|---|
| 2,893,919 | 7/1959 | Opderbeck et al. | |
| 4,048,018 | 9/1977 | Coughlin | 435/175 |
| 4,127,447 | 11/1978 | Griffith et al. | 435/162 |
| 4,209,591 | 6/1980 | Hendriks | 435/813 |
| 4,220,721 | 9/1980 | Ernest et al. | 435/162 |
| 4,242,455 | 12/1980 | Muller et al. | 435/162 |
| 4,266,029 | 5/1981 | Branner-Jorgensen | 435/176 |
| 4,268,419 | 5/1981 | Rohrback | 252/430 |
| 4,271,269 | 6/1981 | Franzmann et al. | 435/176 |
| 4,304,858 | 12/1981 | Wandrey et al. | 435/288 |
| 4,350,765 | 9/1982 | Chibata et al. | 435/162 |
| 4,350,767 | 9/1982 | Zimmerman et al. | 435/815 |
| 4,355,108 | 10/1982 | Gaddy et al. | 435/165 |

OTHER PUBLICATIONS

Phaff et al., "The Life of Yeasts," Harvard V. Press, 1978, pp. 138, 139.
Wingard et al., "Applied Biochemistry & Bioengineering," vol. 1, Immobilized Enzyme Principles Academic Press 1976, pp. 204-208, 298-304.
CRC Immobilized Enzymes, CRC Press 1975, pp. 124, 125, 126, 161.
Kitajima et al., Bull. Chem. Soc. Japan, vol. 44, 3201-3202, (1971).

Primary Examiner—William F. Smith
Attorney, Agent, or Firm—Fitch, Even, Tabin & Flannery

[57] ABSTRACT

Methods and apparatus are provided for the enzymatic production of ethanol from fermentable sugars. A complete sequence of enzymes for catalyzing the conversion of fermentable sugars to ethanol is retained in a plurality of reaction zones. Fermentable sugar solution is sequentially passed through the zones, and ethanol is recovered from the last zone. Necessary coenzymes and cofactors are added to the solution in the various zones, and means are provided for recovering and, if necessary, modifying the coenzymes prior to reintroduction in the various zones.

18 Claims, 6 Drawing Figures

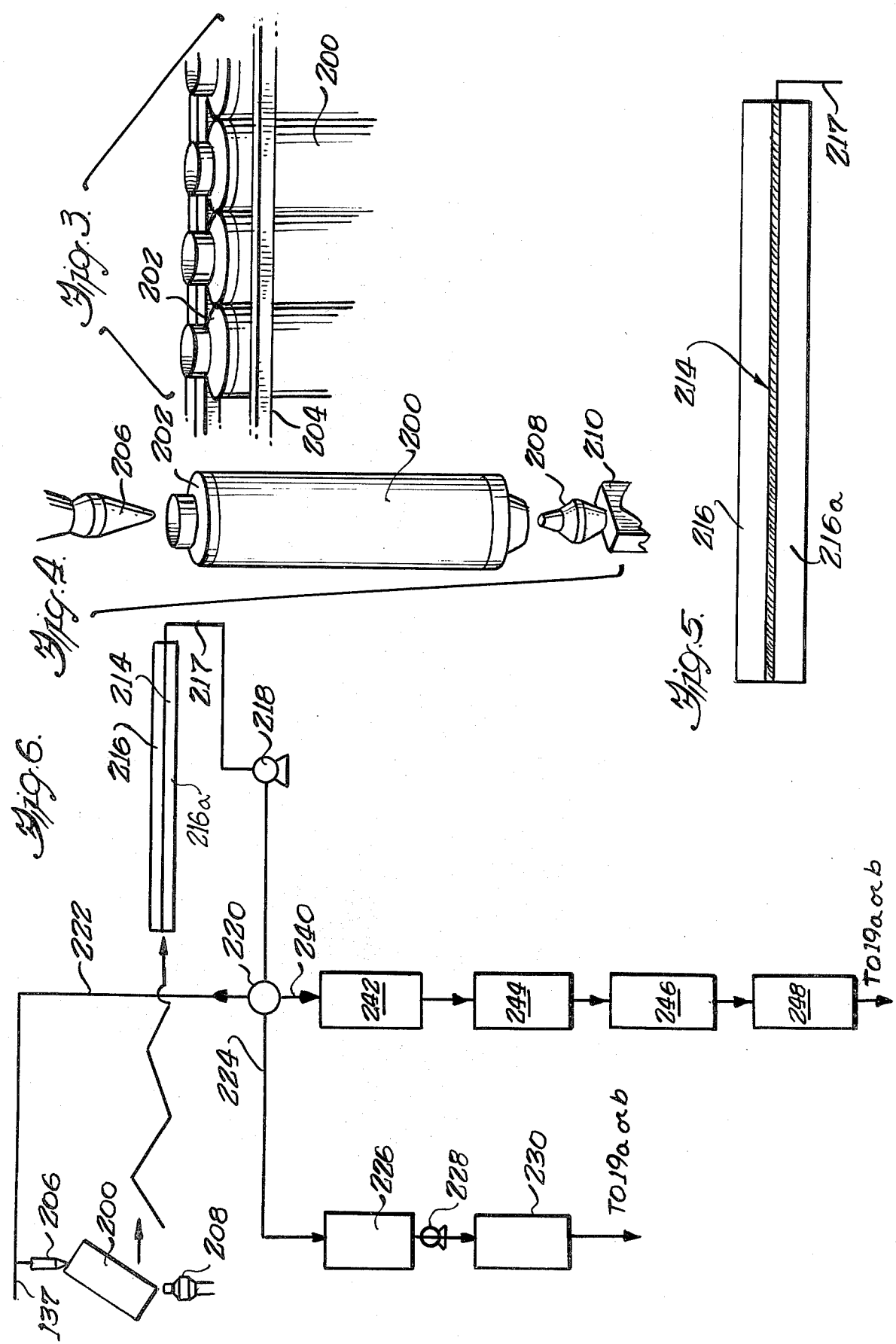

METHODS AND APPARATUS FOR ENZYMATICALLY PRODUCING ETHANOL

The present invention relates generally to the production of ethyl alcohol from fermentable sugars and more particularly to in vitro fermentation processes.

BACKGROUND OF THE INVENTION

With the ever increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol-powered automobiles have averaged a 5% reduction in fuel compared to unleaded gasoline powered vehicles and have emitted one-third less carbon monoxide than the latter. Nations having developing economies where proven domestic petroleum reserves are limited, making the reduction in consumption of petroleum-based fuels particularly critical, such as India and Brazil, have increasingly emphasized the production of alcohol from vegetative sources. The most common such operation employs cane sugar in a fermentation-distillation operation which conveniently utilizes the bagasse by-product as a fuel source.

In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The fermentation of sugar to alcohol is many thousands of years old. It is almost equally as old to first convert carbohydrates (polysaccharide) to simple sugars (monosaccharide) and then to convert the sugars to alcohol. The various operations in processes for obtaining ethanol from such recurring sources as cellulose, cane sugar, amylaceous grains and tubers, e.g., the separation of starch granules from non-carbohydrate plant matter and other extraneous substances, the acid and/or enzymatic hydrolysis of starch and/or cellulose to fermentatable sugar (saccharification), the fermentation of sugar to a dilute solution of ethanol ("beer") and the recovery of anhydrous ethanol by distillation, have been modified in numerous ways to achieve improvements in product yield, production rates and so forth. Numerous processes for the acid hydrolysis of cellulose and starch to provide fermentable saccharides are known, e.g., U.S. Pat. Nos. 3,484,287 and 4,137,654. Numerous acid cellulose hydrolysis processes are known, e.g., U.S. Pat. Nos. 4,029,515; 4,242,455; and 4,093,516.

The enzymatic hydrolysis of various fermentatable polysaccharides has been addressed, for example, in U.S. Pat. Nos. 2,893,919; 3,418,211; 3,972,755 and 4,220,721. Specifically involved in these hydrolysis techniques are the extracted enzymes, glucamylase and cellulase. Methods of enzymatic hydrolysis of cellulosic materials are also known. These different techniques yield a fermentatable slurry composed largely of the monosaccharide d-glucose which is then introduced into known fermentation systems to facilitate conversion to ethanol. Enzymatic methods are also known which hydrolyze disaccharides, such as maltose, lactose and sucrose, which may be hydrolyzed into sugar monomers by maltase, lactase and sucrase.

Recently, sophisticated industrial processes have been developed for more efficiently utilizing yeast and similar microorganisms in fermentation, e.g., U.S. Pat. Nos. 3,705,841, 3,737,323 and 3,940,492. Modern fermentation techniques are described in Cysewski, et al. *Biotechnology and Bioengineering*, Vol. XX pp. 1421-1444 (1978). The fermenting microorganisms utilize nutrients present in a fermentation liquor and convert them to energy and cellular material as well as waste products such as carbon dioxide and ethanol.

In spite of the fact that fermentation is well understood, simple in its application and may utilize otherwise wasted biomass as a starting material, the commercial production of ethanol by fermentation for use other than in medicines or for alcoholic beverages is yet of marginal economic value. In countries, such as the United States, where the cost of gasoline is relatively inexpensive, tax concessions have been necessary in order to make ethanol-petroleum fuel mixtures commercially acceptable.

For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of ethanol as an economically viable replacement for petroleum-based chemicals. To date, however, relatively little concern has been given to the energy requirements for manufacturing ethanol from biomass, and consequently, little effort has been made to minimize the thermal expenditure for carrying out any of the discrete operations involved in the manufacture of ethanol from vegetative sources.

The average yield from known fermenter systems is approximately 12% of the total weight of the fermenter solution or total substrate available. This roughly represents that portion of the sugar molecules remaining, in the form of alcohol, after degrading the sugar to produce energy. Thus, alcohol is a final waste product in the production of biological energy. In addition to producing energy, the catalytic pathway furnishes intermediates utilized by the cell in producing macro-molecules (nucleotides, polypeptides, cellulose etc). Those intermediates diverted along alternate enzymatic pathways do not become alcohol. A recent study implied a calculated maximum ethanol yield through fermentation of 40% of the fermentable sugar. The underlying fact is that somewhere between 60% and 88% of the fermentable sugar is consumed by the microorganism and not converted to ethanol.

Another important limitation to the use of fermentation-produced alcohol is its low concentration. Yeast will convert sugar to alcohol until the fermentated liquor contains up to about 12-14% ethanol at which point the waste product, i.e., ethanol, inhibits the yeast culture. In order to obtain more concentrated ethanol, the fermenter mash is subjected to extensive distillation. This requires extensive thermal energy. It is roughly calculated that it takes three units of thermal energy to produce one unit of thermal energy in the form of ethanol by current fermentation procedures. While this thermal energy may be obtained at least in part from burning otherwise unusable material, such as waste biomass, and while the end product, substantially pure ethanol, is in a highly useful form, it is clear that a much more energy efficient process is desirable.

Further, the fermentation process yields waste products in the form of excess culture material which must be disposed of in an environmentally acceptable way. Expense is also involved in limiting emmission from burning material to produce heat for distillation.

In vitro enzymatic conversion of fermentable sugars, such as glucose and fructose, to ethanol eliminates some of the problems of fermentation procedures. Without additional enzymes, the intermediate products of fermentation are not diverted to side paths for incorporation into cellular material, and substantially increased percentage yields of ethanol may be achieved. The percentage of ethanol in solution is not limited by the need to maintain a viable culture, and hence, a "beer" highly concentrated in ethanol may be produced. Of course, no waste culture material is produced.

Despite its advantages, enzymatic fermentation has its own disadvantages which, heretofore, have counterindicated its use. The primary reasons for the scant conceptualization of complex in vitro enzymatic systems of industrial application has been expensive enzyme production requirements and limited enzyme availability. Whether enzymes are obtained from animal tissues or microorganism culture, their extraction and even partial purification are tedious and expensive. In addition, the coenzymes needed for the enzymatic processes to proceed are themselves expensive. Any fermentation system which spends substantial amounts of enzymes and/or coenzymes is likely to be prohibitively expensive in spite of a significantly higher yield of ethanol.

The enzymatic pathway by which yeast and some other microorganisms convert glucose to ethanol is well known. This pathway is identical to the glycolytic pathway by which animals metabolize glucose except that, in yeast or similar microorganisms, pyruvic acid is decarboxylized to acetaldehyde and then reduced to ethanol, whereas, in animals, pyruvic acid is reduced to lactic acid. Although the corresponding enzymes required to catalyze each step of sugar metabolism differ from species to species, corresponding (in function) enzymes may be freely substituted for each other in in vitro systems, and various plant and animal enzymes may be used to complete the enzyme chain which converts glucose to ethanol.

Various glycolytic enzymes are used to reproduce portions of the glycolytic pathway, such as in medical enzyme assays in which the product of the enzyme being measured is further enzymatically processed into an easily detectable compound. It is now recognized that glucose may be converted to ethanol in vitro by the full contingent of fermentation pathway enzymes and appropriate cofactors and coenzymes. It is realized that fermentation by an enzymatic process, in the absence of enzymes which would lead to intermediate products along the many alternative pathways present in viable organisms, will result in a higher yield of ethanol per amount of sugar substrate. However, the high cost of the enzymes has strongly counterindicated enzymatic fermentation, and enzymatic fermentation is heretofore unknown as an industrial process for the production of ethanol.

Recent developments have promised to reduce the cost of producing enzymes and thus increase the feasability of enzymatic processes. Some enzymes are produced extracellularly by microorganisms that are available in large quantities and are used in various industrial processes. With the advent of genetic modification as a research and processing tool, the potential exists for producing the enzymes required in fermentation much more cheaply.

Currently, useful techniques are also available to reduce the cost of enzyme use by prolonging the usefulness of the enzymes. Enzymes are catalytic in nature, i.e., they are not used up in the reaction, and in biological systems, the enzyme molecules are used repeatedly. Whereas in vitro systems, such as medical assays, have been generally wasteful of enzymes, techniques are now available to immobilize enzymes so that they are not discarded with the effluent but continue to catalyze reactions for extended periods of time. Techniques, i.e., ultrafiltration, have also been developed for efficiently removing free enzyme from a product stream so that the enzyme may be recirculated through the system.

The choice between use of the soluble free enzyme and the immobilized enzyme depends on the cost of the enzyme, the nature of the conversion process, and the relative operational stabilities of the two forms. The additional costs of enzyme isolation and immobilization must be balanced against the potential advantages of isolated enzymes. Compared to microorganisms, isolated enzymes may give higher yields of the desired product with less contamination by side products and cellular material. Also there is the possibility of modifying the kinetics of an enzyme when it is immobilized. In current industrial practice, immobilized enzymes are reused at least 10–15 times in batch processes (or the equivalent time in continuous processes) and in some cases for much longer (over 50 times or the equivalent). So far, immobilized cells normally have been used for fewer batches or shorter periods before being discarded. By their nature, some food processes, such as meat tenderization and baking, involve the addition of the enzymes at the final processing stage, making reuse impossible. In some instances, the ability to remove the immobilized enzyme from the product stream, ensuring minimal contamination by protein, and the ability to modify the reaction kinetics influence the choice, but the main factor is the operational stability of the enzyme. If the enzyme can be stabilized by modification or immobilization, reuse of the enzyme is worthwhile.

SUMMARY OF THE INVENTION

A production scale process for the enzymatic conversion of sugars to ethanol utilizes the enzymes of the glycolytic pathway. The enzymes are either immobilized or recovered and recycled through the system to provide for efficient use of the enzymes. The system provides for continuous flow of a sugar substrate solution into the system where the sugar is enzymatically converted to ethanol. The effluent or "beer" from the system contains highly concentrated ethanol. The system utilizes a plurality of successive reaction chambers containing groupings of successive glycolytic-fermentation-pathway enzymes which are advantageously grouped together according to similarities in maximal reaction conditions, free energies of the grouped enzyme catalyzed reactions and compatability with required coenzymes. In addition to efficient use of enzymes, various coenzymes are recovered and recycled in the system. The excess ATP which is generated in the yeast glycolytic pathway is converted to ADP for recycling through the system.

BRIEF DESCRIPTION OF THE DRAWINGS

FIG. 3 is a perspective view of a magazine of adsorption chambers used in recovering and recycling material used in the system;

FIG. 4 is an elevation view of one of the adsorption chambers preparatory to being connected in-line in the fermentation system;

FIG. 5 is a desorption chamber in which spent adsorption material from the chamber of FIG. 4 is regenerated and coenzyme is recovered; and FIG. 6 is a schematic of one of the recovering and recycling systems including the chamber of FIG. 4 and the desorption chamber of FIG. 5.

DETAILED DESCRIPTION OF THE PREFERRED EMBODIMENTS

Figure 1:
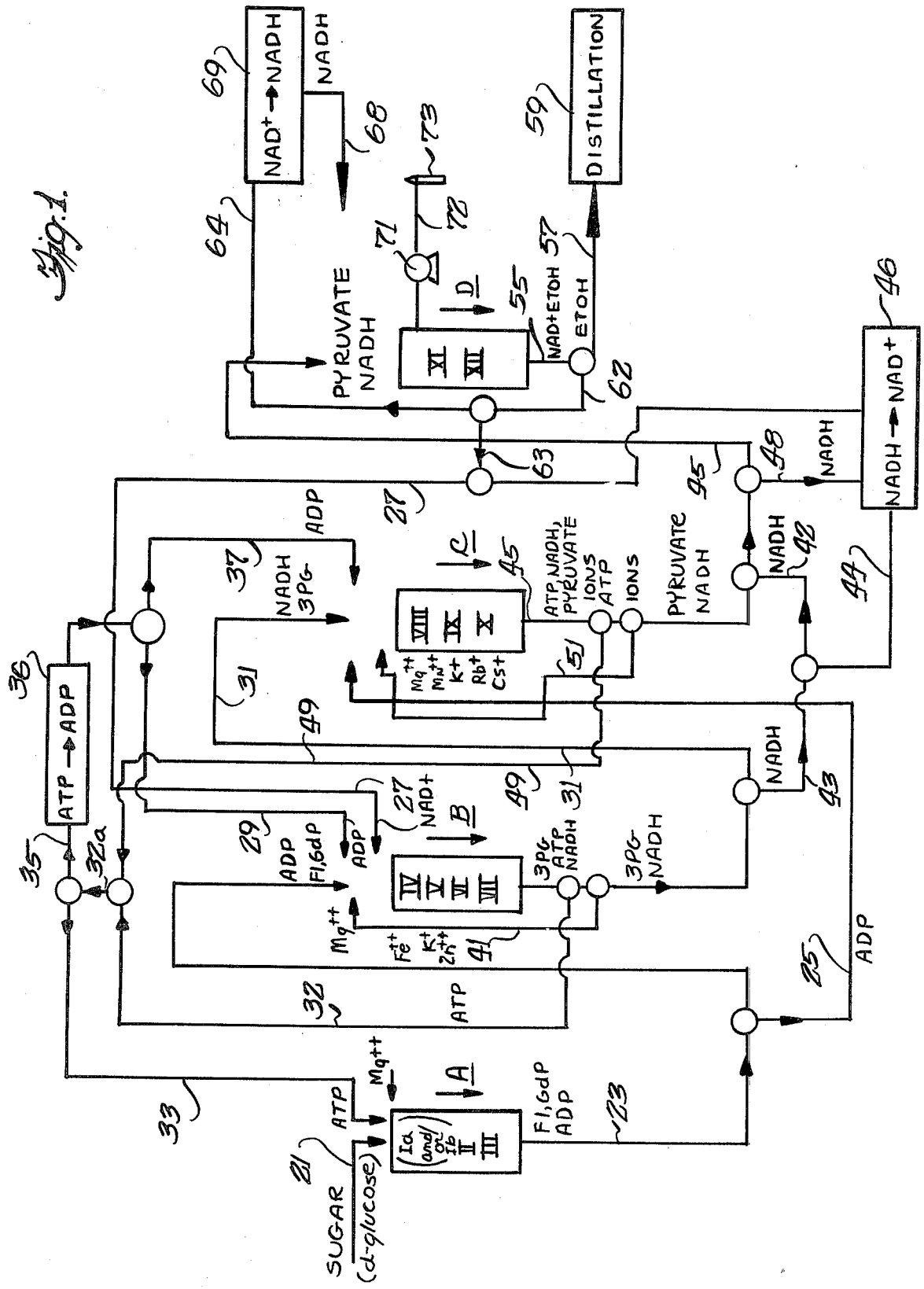
FIG. 1 is a schematic of an enzyme fermentation system embodying various features of the invention.

In accordance with the present invention, sugars are converted to alcohol in an in vitro enzymatic process which is carried out with greater efficiency than the natural fermentation process which utilizes yeast or similar microorganisms. The primary process utilizes only those enzymes in the direct glycolytic fermentation pathways between fermentable sugar monomers and ethanol, thereby eliminating the many enzyme-catalyzed side reactions which occur in vivo in microorganisms. The primary expenditure of enzyme-catalyzed reactions, i.e., the use of costly enzymes, is reduced substantially by immobilizing and/or recycling the enzymes through the system to more fully realize the long-term catalytic capabilities of the enzymes. Further expenditure is reduced through recovery, regeneration and recycling of expensive coenzymes. The concentration of ethanol produced in the solution flowing through the system is not limited to viability requirements of microorganisms and, thus, effluent or "beer", highly concentrated, e.g., up to about 60% by weight ethanol is obtained. Significant energy savings are realized in distillation when the "beer" is initially highly concentrated in ethanol.

In accordance with another aspect of the invention, the rate of ethanol production is increased by grouping the enzymes of the glycolytic fermentation pathway so that the various steps proceed under generally optimal conditions. These groupings recognize the free energies of the several enzyme-catalyzed reactions within each grouping so that the combined steps within each grouping proceed substantially to completion. The effluent from each of the groupings is continuously monitored, and the addition of substrate, cofactors and coenzymes and the environmental conditions are adjusted to maximize the end product of each of the groupings.

In accordance with a further aspect of the invention, apparatus is provided for efficiently removing and recycling coenzymes in a continuous flow system. A plurality of chambers having coenzyme adsorbing material are successively inserted in-line, whereby coenzyme is continuously adsorbed until the adsorbing material is saturated. Material from the spent adsorbing chambers is removed to a porous bed where an electrical current is used to draw coenzyme from the adsorbing material and through the porous bed. The recovered coenzyme is regenerated, if necessary, and returned to the system, and the cleansed adsorbing material is used to repack adsorbing chambers.

So that the invention will be more fully understood, the methods and systems of the invention will now be described in greater detail.

In preparation for enzymatic fermentation, fermentable sugars are obtained from an aqueous slurry of carbohydrate polymer particles, such as starch granules and/or cellulose chips, fibers, etc., by subjecting the slurry to thermochemical (acid and pressurized steam) or enzymatic hydrolysis. At least about 60% by weight conversion and preferably at least about 80% by weight conversion of the carbohydrate polymer to fermentable hydrolysate is achieved without appreciable conversion of carbohydrate polymer to nonfermentable products. Among the sources of carbohydrate polymers which can be employed herein are cellulosic materials, such as wood chips, sawdust, bark and plant fiber, the cellular tissue of root crops, such as manioc, potatoes, yams, turnips, beets, carrots and the like, and starch from grains, such as corn, rice, wheat, milo and their mixtures. The carbohydrate polymer slurry can contain from about 20 to 50 weight percent dry substance (D.S.) or more, and preferably contains from about 30% to 40% D.S. to facilitate pumping. The slurry can also contain other components of the source material, such as water soluble proteins, fats, sugars and minerals and or water insoluble materials, such as minute amounts of gravel, etc.

The carbohydrate polymer can be extracted from the source material employing any of the known and conventional procedures. Acidification of the carbohydrate polymer slurry can be accomplished with any strong inorganic acid, i.e., an acid having a pKa value of at least about 2.0 or less. Examples of strong inorganic acids which can be used include nitric acid, sulfuric acid, hydrochloric acid and phosphoric acid. Neutralization of the acid following conversion of the carbohydrate polymer to fermentable sugar can be accomplished with any suitable base. Conversely, enzymatic hydrolysis of carbohydrate polymers will also yield soluble saccharide monomers which can then be collected from the slurry using a flow-through ultrafiltration system. Maximum solubility for fermentable monomers in the temperature range described herein is in the area of 60%. Therefore, the fermentable hydrolsate is diluted to a lesser concentration, preferably in the range of 20-40% unless variables within the system permit efficient utilization at 60-80%. Following conversion of the carbohydrate polymer to fermentable sugar, the latter is introduced to the in vitro conversion process. Hydrolysis of the above-mentioned fermentable sugars generally yields the carbohydrate monomers glucose and fructose. Both of these carbohydrates will enter the in vitro process at the same point.

The in vitro conversion process is a system by which an appropriately prepared substrate solution (containing a high concentration of carbohydrate material) is made to pass through a continuous flow process in which the environmental and physical parameters of the solution containing the suspended substrate are mechanically controlled, adjusted and monitored to accomodate the specific requirements of each enzyme reaction chamber.

The system utilizes the specific fermentation enzymes in reaction chambers in concentrations and in their proper sequence so as to accomodate a batch or continuous flow multistep conversion of fermentable sugars and other hydrocarbons to ethanol on an industrial scale.

The catalytic conversions accomplished by the particular enzymes described in Table I below are cited in the examples herein; however, the invention is not necessarily limited to enzymes so designated.

TABLE I

| | Preferred Name | I.D. Number |
|---|---|---|
| 1b. | Glucokinase | 2.7.1.2 |
| 1b. | Hexokinase | 2.7.1.1 |
| 2. | Hexose isomerase | 5.3.1.9 |
| 3. | 6-Phosphofructokinase | 2.7.1.11 |
| 4. | Aldolase (Fructose diphosphate aldolase) | 4.1.2.13 |
| 5. | Triosephosphate isomerase | 5.3.1.1 |
| 6. | Glyceraldehydephosphate dehydrogenase | 1.2.1.12 |
| 7. | Phosphoglycerate kinase | 2.7.2.3 |
| 8. | Phosphoglyceromutase | 2.7.5.3 |
| 9. | Enolase | 4.2.1.11 |
| 10. | Pyruvate kinase | 2.7.1.40 |
| 11. | Pyruvate decarboxylase | 4.1.1.1 |
| 12. | Alcohol dehydrogenase | 1.1.1.1 |

Enzyme identification numbers are recommended by the Nomenclature Committee of the International Union of Biochemistry. The sequential enzymatic breakdown of carbohydrates is well understood to those skilled in the Biochemical Sciences. It is generally agreed that the in vivo catabolism of various carbohydrates by this enzymatic sequence is specifically accomplished by the organism (multi or single celled) for the principal purpose of providing substrates or building blocks used in the synthesis of other organic compounds or for the generation of biochemical energy in the form of adenine triphosphate (ATP) and nicotine adenine dinucleotide (NADH) (reduced) and not specifically for the generation of ethanol and carbon dioxide which are, in fact, waste products of these metabolic activities. Therefore, a system of this in vitro design serves a radically different purpose from the in vivo system in that the primary end products (ethanol and carbon dioxide) of the in vitro system are generated without branch points which would deplete the substrate or intermediates.

A description of the biomodification of d-glucose (the primary fermentative carbohydrate) through this in vitro enzymatic system is provided with reference to Table II below in which the reactions (designated by roman numerals) are summarized with emphasis on the substrate intermediate enzyme (designated by arabic numerals) interaction.

TABLE II

| | | | | $\Delta G$ | $\Delta G^{o\prime}$ | pH | Temp. (C.) |
|---|---|---|---|---|---|---|---|
| (I) | glucose + ATP | (1b) hexokinase or (1a) glucokinase → | glucose 6-phosphate + ADP + H$^+$ | −4.0 | −8.0 | 8.5 | 25° |
| (II) | glucose 6-phosphate | (2) phosphoglucose isomerase → | fructose 6-phosphate | +0.4 | +4.0 | 8.3 | 30° |
| (III) | fructose 6-phosphate + ATP | (3) phosphofructokinase → | fructose 1,6-diphosphate + ADP + H$^+$ | −3.4 | −3.4 | 8.0 | 37° |
| (IV) | fructose 1,6-diphosphate | (4) aldolase → | dihydroxyacetone phosphate + glyceraldehyde 3-phosphate | +5.7 | −5.3 | 7.4 | 25° |
| (V) | dihydroxyacetone phosphate | (5) triosephosphate isomerase → | glyceraldehyde 3-phosphate | +1.8 | −0.3 | 7.6 | 25° |
| (VI) | glyceraldehyde 3-phosphate + Pi + NAD$^+$ | (6) glyceraldehydephosphate dehydrogenase → | 1,3-diphosphoglycerate + NADH + H$^+$ | +1.5 | +0.6 | 7.6 | 25° |
| (VII) | 1,3-diphosphoglycerate + ADP | (7) phosphoglycerate kinase → | 3-phosphoglycerate + ATP | +4.5 | +0.3 | 6.9 | 25° |
| (VIII) | 3-phosphoglycerate | (8) phosphoglyceromutase → | 2-phosphoglycerate | +1.1 | +0.2 | 7.4 | 25° |
| (IX) | 2-phosphoglycerate | (9) enolase → | phosphenolpyruvate + H$_2$O | +0.4 | −0.8 | 7.4 | 25° |
| (X) | phosphoenolpyruvate + ADP + H$^+$ | (10) pyruvate kinase → | pyruvate + ATP | −7.5 | −4.0 | 7.6 | 37° |
| (XI) | pyruvate | (11) pyruvate decarboxylase → | acetaldehyde + CO$_2$ | −7.0 | −4.0 | 6.0 | 25° |
| (XII) | acetaldehyde + NADH + H$^+$ | (12) alcohol dehydrogenase → | ethanol + NAD$^+$ | −7.2 | −4.0 | 8.8 | 25° |

The first of two phosphate "priming" reactions in this system requires the use of ATP. In step (I) the neutral d-glucose molecule is prepared for the subsequent enzymatic steps by its phosphorylation to a negatively charged molecule with the concomitant conversion of ATP to ADP. The phosphorylation of d-glucose at the 6-position using ATP as the phosphate donor to yield d-glucose 6-phosphate is catalyzed by two types of enzymes, hexokinase and glucokinase, which differ in their sugar specificity and affinity for d-glucose. Hexokinase is the more widely distributed and is the enzyme normally employed by most living cells. It catalyzes the phosphorylation not only of d-glucose but also of many other hexoses and hexose derivatives, including d-fructose, d-mannose, and d-glucosamine; it has a higher affinity for aldohexoses than for ketohexoses. Hexokinases are found in yeast and bacteria and in many animal and plant tissues. Yeast hexokinase has been crystallized (mol wt 96,000). The second type of glucose-phosphorylate enzyme, glucokinase, phosphorylates only d-glucose and does not act on other hexoses. Glucokinase has a much higher $K_M$ for d-glucose ($K_M = 100$ mM). It differs from hexokinase in another respect: it is not inhibited by glucose 6-phosphate. Glucokinase is present in liver, where it predominates over hexokinase. Where the sugar substrate contains significant amounts of sugar monomers other than glucose, it is preferred that hexokinase rather than glucokinase be used. However, other enzymes such as fructokinase may be used in conjunction with glucokinase to phosphorylate non-glucose sugar monomers.

Both hexokinase and glucokinase require a divalent cation or ($Mg^{++}$ or $Mn^{++}$), which first combines with ATP to form the true coenzyme substrate, $MgATP^{++}$ or $MnATP^{++}$. Hexokinase is inhibited by certain sulfhydryl reagents. The phosphorylation of glucose by either hexokinase or glucokinase is not reversible under intracellular conditions.

Glucose phosphate isomerase, which has been isolated from muscle tissue in highly purified form, catalyzes the isomerization of glucose 6-phosphate to fructose 6-phosphate, (reaction II). The reaction proceeds readily in either direction and is reversible in the cell. Glucose phosphate isomerase is specific for glucose 6-phosphate and fructose 6-phosphate.

In the second of the two priming reactions (Reaction III) of the in vitro process, a second molecule of ATP is required to phosphorylate fructose 6-phosphate in the 1 position to yield fructose 1,6-diphosphate.

$Mg^{++}$ is required, presumably because the true substrate is $MgATP^{++}$. Although fructose 6-phosphate is the specific phosphate acceptor in the reaction, UTP and ITP may replace ATP as phosphate donors. Phosphofructokinase has multiple allosteric modulators. It is inhibited by high concentrations of ATP, citrate, and long-chain fatty acids but is stimulated by ADP or AMP. Therefore, whenever the cell has a high concentration of ATP, or whenever other fuels such as fatty acids or citrate are available, 6-phosphofructokinase is inhibited. Conversely, whenever the [ADP+AMP/ATP] ratio is optimally high and AMP and ADP thus predominant, or whenever the concentration of other molecules such as citrate or fatty acids is low, 6-phosphofructokinase activity is stimulated. Thus, the kinetic behavior of 6-phosphofructokinase is very complex. The positive and negative allosteric modulators of this enzyme vary from one cell type to another under in vivo conditions. The 6-phosphofructokinase reaction is essentially irreversible in vivo; the literature indicates that most regulator enzymes catalyze irreversible reactions.

Cleavage of fructose 1,6-diphosphate to dihydroxyacetone phosphate and glyceraldehyde 3-phosphate (reaction IV) is catalyzed by fructose diphosphate aldolase, which is easily isolated in crystalline form from rabbit-muscle extracts. The catalyzed reaction is a reversible aldol condensation, yielding the two different triose phosphates. Although the ($\Delta$) G°' of this reaction is strongly positive under isolated in vitro conditions, it readily proceeds in the forward directions under controlled conditions.

Typical of the fructose diphosphate aldolases found in higher animals and plants, often called class 1 aldolases, is the one isolated from skeletal muscle, which has a molecular weight of 160,000 and contains four subunits. It also contains a number of free —S—H groups, some of which are essential for catalytic activity. Class 1 fructose diphosphate aldolases occur in different isoenzyme forms. In the tissues of the rabbit there are three major forms, aldolase A, predominant in muscle, aldolase B in the liver, and aldolase C in the brain. All contain four polypeptide subunits which differ in amino acid composition.

The fructose diphosphate aldolase found in bacteria, yeasts, and fungi (class II aldolases) differ from class 1 forms in containing a specific divalent metal ion, usually $Zn^{2+}$, $Ca^{2+}$ or $Fe^{2+}$; they also require $K^+$. Their molecular weight is about 65,000 or less than one-half that of the animal enzymes. They function by a different mechanism than class I aldolases; they do not form Schiff's base intermediates.

Only one of the two triose phosphates (glyceraldehyde 3-phosphate) formed by reaction IV can be directly degraded in the subsequent reactions of this system. The other, dihydroxyacetone phosphate, is reversibly converted to glyceraldehyde 3-phosphate by the enzyme triosephosphate isomerase (reaction V). Dihydroxyacetone phosphate constitutes over 90% of an equilibrium mixture of the two triose phosphates. Thus, the "pulling" potential of the following enzymes must be utilized to push this reaction in the forward direction.

The enzyme catalyzing the oxidation of glyceraldehyde 3-phosphate (reaction VI) usually called glyceraldehydephosphate dehydrogenase (3-phosphoglyceraldehyde dehydrogenase is also correct), is easily isolated in crystalline form (mol wt 140,000) from rabbit muscle or yeast. It contains four identical subunits, each consisting of a single polypeptide chain of some 330 residues, the amino acid sequence of which has been deduced.

In this reaction, the aldehyde group is oxidized to the oxidation level of a carboxyl group. However, instead of a free carboxylic acid, the reaction yields a mixed anhydride of the carboxyl group of 3-phosphoglyceroyl phosphate which is a high-energy phosphate compound having more negative standard free energy of hydrolysis than ATP.

The other important component of this reaction is $NAD^+$, the oxidized form of nicotinamide adenine dinucleotide, which accepts electrons from the aldehyde group of glyceraldehyde 3-phosphate. $NAD^+$ is now known to be one of the components of cozymase, the heat-stable fraction required for alcoholic fermentation found in the early experiments of Harden and Young. $NAD^+$ serves as a carrier of electrons from the electron donor D-3 phosphoglyceraldehyde to pyruvate, which is formed later in this process. The overall reaction has a small positive value of $(\Delta)G°'$ and thus proceeds readily in either direction depending on the concentration of the reactants and products.

The oxidation of glyceraldehyde 3-phosphate by $NAD^+$ is a highly exergonic process that would normally proceed far to the right, starting from 1M concentrations of reactants, whereas the formation of 1,3 diphosphoglycerate from 3-phosphoglyceraldehyde and phosphate is highly endergonic and would not proceed as written. However, in the overall enzymatic reaction, the endergonic process is obligatorily coupled to the exergonic process, so that the energy released on oxidation of the aldehyde is conserved in the form of the high energy acyl phosphate group of 1,3 diphosphoglycerate (3-phosphoglyceroyl-phosphate). Each of the enzyme's four identical subunits contains an active catalytic site to which is bound a molecule of NAD+.

Glyceraldehyde 3-phosphate dehydrogenase is an allosteric enzyme; its major effector being NAD+, which is also one of its substrates. Binding of the first molecule of NAD+ to one of the its binding sites diminishes the affinity of the other subunits for NAD+ but enhances their instrinsic activity. This is an example of an allosteric enzyme showing negative cooperativity. Phosphoglyceraldehyde dehydrogenase is inhibited by heavy metals as well as by alkylating agents, such as iodoacetate. For this and other reasons, it has been concluded that a sulfhydryl group in the active site is essential for catalytic activity. The enzyme binds the oxidized form of the coenzyme NAD+ first, in a reaction in which the essential sulfhydryl group becomes sterically masked. In the next step, the aldehyde group of the substrate forms a thiohemiacetal linkage with the sulfhydryl group. The enzyme then catalyzes hydrogen transfer from the covalently bound glyceraldehyde 3-phosphate to the bound NAD+, forming a thioester between the enzyme sulfhydryl group and the carboxyl group of the substrate; this form of the enzyme is called the acyl-enzyme. The NADH then leaves the enzyme active site in exchange for a molecule of free NAD+ from the medium. The acyl group is then transferred from the sulfhydryl group of the enzyme to inorganic phosphate to form 3-phosphoglyceroyl phosphate, the oxidation product. The free oxidized form of the enzyme is now ready for another catalytic cycle.

3-phosphoglyceroyl phosphate, formed in the preceeding reaction, now reacts (reaction VII) enzymatically with ADP, with transfer of the acyl phosphate group to ADP and formation of 3-phosphoglycerate catalyzed by phosphoglycerate kinase. This reaction is highly exergonic and serves to "pull" the preceding reaction toward completion. The phosphate-transferring enzyme has an extremely high affinity for 3-phosphoglyceroyl phosphate. The overall equation for the two reactions, the first involving oxidation of glyceraldehyde 3-phosphate to 3-phosphoglyceroyl phosphate and the second involving transfer of the acyl phosphate group to ADP catalyzed by phosphoglycerate kinase, is Glyceraldehyde
3-phosphate+Pi+ADP+NAD+→3-phosphoglycerate+ATP+NADH+H+

$G = -3.0$ kcal mol$^{-1}$

The conversion of 3-Phosphoglycerate to 2-phosphoglycerate (reaction VIII), is catalyzed by the enzyme phosphoglyceromutase. Mg$^{2+}$ is essential for this reaction, which involves transfer of the phosphate group from the 3 to the 2 position of glyceric acid. The reaction has only a small standard free-energy change and is freely reversible in the cell.

There are two forms of phosphoglyceromutase; the form in animal tissues appears to require 2,3-diphosphoglycerate as an intermediate, according to the equation 2,3-Diphosphoglycerate+3-phosphoglycerate→2-phosphoglycerate+2,3-diphosphoglycerate.

The conversion of 2-phosphoglycerate to phosphoenolpyruvate is the second reaction (reaction IX) of the in vitro sequence in which a high-energy phosphate compound is generated. It is catalyzed by enolase. Enolase (mol wt 85,000) has been obtained in pure crystalline form from several sources. It has an absolute requirement for a divalent cation (Mg$^{2+}$ or Mn$^{2+}$) which makes a complex with the enzyme before the substrate is bound. The enzyme is strongly inhibited by fluoride, particularly if phosphate is present, the inhibitory species being the phosphofluoridate ion, which forms a complex with Mg$^{2+}$. Although the reaction catalyzed by enolase is formally an elimination of a molecule of water from carbon atoms 2 and 3 of 2-phosphoglycerate, it may also be regarded as an intramolecular oxidoreduction, since the removal of water causes carbon atom 2 to become more oxidized and carbon atom 3 more reduced. Despite the relatively small standard free-energy change in this reaction, there is a very large change in the standard free energy of hydrolysis of the phosphate group of the reactant and product, that of 2-phosphoenolpyruvate about $-4.2$ kcal/mol and that of phosphoenolpyruvate about $-14.8$ kcal/mol. Evidently there is a large change in the distribution of energy within the 2-phosphoglycerate molecule when it is dehydrated to phosphoenolpyruvate.

The transfer of the phosphate group from phosphoenolpyruvate to ADP (reaction IX), yielding free pyruvate is catalyzed by the enzyme pyruvate kinase which has been obtained in pure crystalline form (mol wt 250,000). The reaction is highly exergonic and it has been found to be irreversible under intracellular conditions. The enzyme requires Mg$^{2+}$ or Mn$^{2+}$, with which it must form a complex before binding the substrate. Ca$^{2+}$ competes with Mn$^{2+}$ or Mg$^{2+}$ and forms an inactive complex. The enzyme also requires an alkali-metal cation, which may be K+, Rb+, or Cs+; K+, as the physiological activator. It is believed that the binding of K+ causes a conformataional change of the enzyme to produce a more active form. Pyruvate kinase in mammals is a regulatory enzyme and occurs in different forms in various tissues. The L, or liver, form is activated by fructose 1,6-diphosphate and by high concentrations of phosphoenolpyruvate but is inhibited by ATP, AMP, and citrate and alanine. It is also inhibited by long-chain fatty acids and acetyl-CoA. The M, or muscle, form is not activated by fructose 1,6-diphosphate but is inhibited by phenylalanine.

Pyruvate is decarboxylated to acetaldehyde and CO$_2$ (reaction XI) by the enzyme pyruvate decarboxylase, which is not present in animal tissues. The decarboxylation of pyruvate to form acetaldehyde and CO$_2$ is essentially irreversible due to removal of CO$_2$ from the solution. Pyruvate decarboxylase requires Mg$^{2+}$ and has a tightly bound coenzyme, thiamin pyrophosphate.

In the final step of in vitro alcoholic production, acetaldehyde is reduced to ethanol (reaction XII), with NADH+H+ furnishing the reducing power, through the enzyme alcohol dehydrogenase.

Ethanol and CO$_2$ are thus the end products of this process. The overall equation of alcoholic production can therefore be written:

Glucose+2Pi+2ADP→2
ethanol+2CO$_2$+2ATP+2H$_2$

Internally cycled coenzyme: nicotinamide adenine dinucleotide
Externally cycled coenzyme: adenine diphosphate The above-described enzymes constitute the basic catalysts for this in vitro process; however, the invention is not necessarily limited to enzymes so designated. Any enzymes capable of converting substrates or intermediates discussed in this process and/or known to be involved in the conversion of fermentable sugars to ethanol and not otherwise substantially affecting the basic direction of this in vitro process falls within the scope of this invention.

The enzymes are preferably used in an immobilized form, although free enzyme can also be used provided they can be maintained within the appropriate reaction chambers, e.g., by ultrafiltration techniques. The processes for enzyme immobilization are familiar to those skilled in the art, as stated hereinabove and consists of reacting a solution of each enzyme with one of a broad range of surface treated or untreated organic and inorganic supports. Included among these are polyacrylamide, ethylenemaleic acid, copolymers, agarose, cellulose, dextran, silica, porous glass beads, charcoal or carbon black, wood and sawdust, hydroxy apatite and aluminum or titanium hydroxide. Enzymes in this form have increased stability, extended life and usefulness and recoverability. In certain cases, immobilized enzymes have substantially higher cataylytic activity than the free enzyme. Reactions employing immobilized enzymes may be run in columns or reaction chambers or other suitable reactors.

The well studied coenzymes, adenine triphosphate (ATP) and nicotine adenine dinucleotide (NAD+), are integral components of this system as identified in the previous enzyme descriptions. The coenzymes serve more as substrates than as prosthetic groups because they bind very loosely to the respective enzymes and help catalyse the substrate conversion action, while being modified themselves. This catalytic assistance is provided, as described previously, on a one-for-one basis of substrate and coenzyme wherein the coenzyme donates or accepts phosphates (ATP) or hydrogen (NAD+) during the conversion of each substrate molecule by the appropriate enzyme. As such, the utilization of these coenzymes constitutes a major complicating factor in this complex system, these coenzymes are added to the various substrate solutions, allowed to interact with the appropriate enzymes and extracted, if necessary, after the solution leaves the reaction chamber. Extraction of these coenzymes is preferably accomplished using affinity binding techniques. The coenzymes isolated in this manner are dissassociated from the affinity matrix using various known techniques, preferably electrophoretic desorbtion and recycled with or without modification through the same or alternate reaction chambers as needed. Coenzymes are modified as required. In the case of ATP/ADP, more ATP is formed in this process than used and therefore must be converted back to ADP. ATP, isolated in the manner described above, is preferably introduced to a subsidiary in vitro system wherein the enzymes which catalyze the conversion of ATP to ADP are contained in a separate reaction chamber sequence and provide the necessary modification step.

The coenzyme nicotinamide adenine dinucleotide, (NAD+) is cycled through the entire modification and remodification (oxidation reduction) sequence within the confines of this proposed in vitro system (without modification) and therefore needs only to be extracted from solution at one point and reintroduced at its original point of entry in the in vitro process. NAD+/NADH recycling systems, which have also been reported in the literature, are utilized for "cleansing" or totally regenerating one form or another of this coenzyme when that function is needed periodically.

Thiamine pyrophosphate is a tightly bound coenzyme to pyruvate decarboxylase and as such does not represent an additional complicating element in this continuous flow system.

The catalytic capabilities of enzymatic proteins have universally been considered in terms of the Michaels Menton equation which generally describes the rate of catalysis. Standard analysis of enzymatic conversion rates have generally been accomplished in a closed system wherein the substrate concentration, though at saturating levels initially, will, as those skilled in the art are aware, be depleted. Another variable not normally introduced into standard kinetic analysis is the complexity of multiple enzyme steps within the same closed or open system. The efficiency of multistep conversion can be greatly enhanced (as much as 400%) over a soluble mixed system by arranging the enzymes in close proximity to each other in a fixed system. Because of these influences, the standard methods for analysis do not provide the most efficient evaluation of a flow-through multienzyme fixed system. Analysis can, however, be accomplished by modifying standard analysis procedures to accommodate these variables. The time course of an enzyme-catalyzed reaction is described by the integrated form of the Michael Menton equation.

$$FS - K \ln(1-F) = KsEct$$

Where F represents the fractional conversion of substrate to product; S is the initial substrate concentration in mM; K is the substrate concentration units required to produce half the maximum reaction velocity (mM); Ks is the specific activity of the enzyme (moles m$^{-1}$ mg$^{-1}$); Ec is the concentration of enzyme (mg cm$^{-3}$); and t is the elapsed reaction time (minutes). Computer simulation of multiple enzyme systems has been accomplished. Because the state of the art for immobilized enzyme kinetics has not yet reached full maturation, the true evaluation of the efficiency of conversion is not universally deciphered. A method for making these determinations has been described.

FIG. 1 generally indicates the preferred groupings of enzymes into reaction chambers containing in total the full complement of enzymes necessary to catalyze a multiple step process, though this process is not limited to these groupings. It is envisioned that the reaction chambers are sequentially connected. Filtering, monitoring, delivery and extraction systems support and maintain reaction efficiency as described in greater detail hereinafter.

The resolved end product of one reaction chamber becomes the primary substrate solution for the next reaction chamber in sequence. Enzyme types contained in reaction chambers may be isolated on separate matricies in a sequential gradient configuration or grouped in multi-enzyme reaction units wherein the enzymes within the reaction chambers are coupled to a matrix, (e.g.) glass beads, in multi-enzyme configuration to allow for the end product of one enzymatic step to be in closest proximity to the subsequent enzyme thereby facilitating maximal saturation of substrate in the enzyme micro environment.

The enzymes used in preparing the system are available from the Sigma Chemical Company (see table 1).

All enzymes from this source are reported to generate maximal catalytic activity at a temperature range of 20° to 40° and a pH range of approximately 6.0 to 8.8.

The in vitro process can potentially be accomplished in a single reaction system as is the case in in vivo systems. A single reaction chamber would not, however, maximize the rate of ethanol production. The optimal conditions, e.g., pH, temperature, differ from reaction to reaction. Coenzymes which catalyze certain of the reactions inhibit others. The other extreme would be to use separate reaction chambers for each of the conversion steps. However, the positive free energy of several of the reactions means that in some cases the equilibrium is shifted far to the left. Such reactions require the driving force of later reactions with negative free energies to remove product and drive the positive free energy reactions to the right.

The preferred embodiment for this process entails the implementation of four reaction chambers A,B,C,D (FIG. 1) which contain the following combinations of enzyme groups: (A) hexokinase (1a) and/or glucokinase (1b), glucose phosphate isomerase or other hexoisomerases (2), phosphofructokinase (3); (B) aldolase (4), triose phosphate isomerase (5), glyceraldehyde 3-phosphate dehydrogenase (6), phosphoglycerate kinase (7); (C) phosphoglycerate mutase (8), enolase (9), pyruvate kinase (10); (D) pyruvate decarboxylase (11) and alchol dehydrogenase (12). These groupings are based on factors such as similarities of reaction conditions, free energy requirements and coenzyme requirements.

In each of the chambers the ADP/ATP and/or the $NAD^+$/NADH coenzyme systems proceed in a single direction. Thus, it is possible to introduce into each chamber controlled amounts of a coenzyme moiety or moieties which serve as substrate for one or more of the grouped reactions. The pyruvate kinase catalyzed reaction, which is inhibited by ATP, is included in group C where ADP is introduced as a coenzyme substrate. Because the ADP/ATP and $NAD^+$/NADH coenzyme systems proceed in a unitary direction in each group, the concentrations of the introduced coenzyme may be used to drive the equilibrium to the right (product) in each chamber. The reactions of three of the four groupings have similar optimal pH's. The optimal pH's of the group A reactions range between 8.0 and 8.5. The optimal pH's of the group B reactions range between 6.9 and 7.6. The optimal pH's of the group C reactions range between 7.4 and 7.6. Although the optimal pH's for group IV reactions are widely divergent, both of the group D reactions have highly negative free energies and proceed readily at pH's intermediate to their individual optimal pH's.

An important consideration in grouping the reactions is the free energy which must be negative for the reactions in a group to proceed toward product formation. The total $(\Delta) G^{o'}$ of a group is a reasonable indication of the degree to which the combined group reactions proceeds to completion, although the actual conditions are not standard, and the real free energy of a reaction group can be adjusted to favor product formation by adjusting various conditions such as pH and substrate concentration. It is particularly important that the last reaction in each of the groups have a high negative free energy in order to drive preceeding reactions, which may have positive or slightly negative free energies, toward product formation. Reaction III (group A), catalyzed by phosphofructokinase, has a high negative free energy and is essentially irreversable. Both of these reactions drive prior positive free energy reactions to completion. In group B, the phosphoglycerate kinase reaction, though reversable, has a high negative free energy change and helps to drive preceeding positive free energy reactions to the right. Both of the reactions of group D have high negative free energies and are essentially irreversable. Reaction XI, proceeds only in a single direction due to loss of $CO_2$ from the system.

The system can accommodate certain variations in the preferred groupings without significant loss of efficiency. Reaction I might be isolated in a separate reaction chamber. Reactions XI and XII might be grouped in separate reaction chambers or might be grouped with group C. On the other hand, free energy requirements mandate certain groupings for efficiency of product formation. Reaction II is driven forward by reaction III. Reactions IV, V and VI are driven forward by reaction VII and reactions VIII and IX are driven forward by reaction X. Reactions IV and V could not be practically separated as it is necessary to convert all of the triose produced in reaction IV to glyceraldehyde 3-phosphate for continuation on the fermentation pathway.

The above-described groupings contemplate the introduction into the system of soluble sugar substrate having a high percentage of glucose monomer. Fructose can be converted to F6P by hexokinase; however, if large amounts of fructose monomer are to be digested, enzymes of the fructose 1-phosphate pathway may be incorporated. Other sugars may also be utilized with the incorporation into the system of appropriate enzymes.

The assays used to analyze the concentrations of the carbohydrates and coenzymes of d-glucose, d-fructose 1,6-phosphate, 3-phosphoglycerate, pyruvate, ethanol, ADP, ATP, $NAD^+$, NADH present in the solutions entering or leaving the four main reaction chambers of the present invention are given below. Both colorimetric and ultraviolet assay analysis can be accomplished using a Gilford system 2600 spectrophotometer equipped with an aspirating thermocuvette and a recorder. The concentration of d-glucose present in solutions entering and leaving reaction chamber A is determined by one of the following methods:

a. colorimetric assay at 425-475 nm using Sigma Chemical Co. assay kit #510 which employs glucose oxidase and peroxidase enzyme and O-Dianisidine as the chromogen.

b. colorimetric assay at 620-650 nm using Sigma Chemical Co. assay kit #635 in which glucose reacts with O-Toluidine glacial acetic acid reagent to yield a blue-green color proportional to the glucose concentration. This reaction is carried out in a boiling water bath.

The amount of fructose 1,6-diphosphate per unit volume leaving reaction chamber A, B and/or entering reaction chamber B is followed with an assay mixture containing a known concentration of the enzyme transaldolase (E.C. 2.2.1.2) (D sedoheptulase 7-phosphate; d-glyceraldehyde 3-phosphate dihydroxacetone transferase), and saturating concentrations of d-erythrose-4-phosphate and the reduced coenzyme NADH (nicotinamide adenine dinucleotide). The changing concentration of NADH as determined at the ultraviolet wave length 340 nm measures the amount of fructose 1,6-diphosphate.

3-phosphoglycerate in the solution recovered from reaction chamber B is determined by adding a sample of that solution to an assay mixture containing a known concentration of 3-phosphoglycerate dehydrogenase and saturating concentrations of the coenzyme nicotinamide adenine dinucleotide (NADH). The rate of reduction to NADH is a measure of the presence of 3-phosphoglycerate as measured by the increase in absorbance 340 nm.

The pyruvate concentration leaving reaction chamber C is determined using Sigma Chemical Company assay kit #726 UV in which pyruvate is converted to lactic acid by lactic dehydrogenase resulting in the oxidation of an equivalent amount of NADH. The decrease in absorbance at 340 nm is proportional to the pyruvate concentration in the sample solution.

The concentration of ethanol leaving the final reaction chamber can be determined prior to distillation using Sigma Chemical Co. analysis kit #331 UV in which ethanol contained in test samples is oxidized by alcohol dehydrogenase with the simultaneous reduction of $NAD^+$ to NADH.

Because the recycling of the coenzymes $NAD^+$ and ATP is an important element of this cost efficient system, the following assays are performed.

Test samples are taken at various stages of this continuous flow system and after ATP is extracted, isolated and (if necessary) converted, the samples are analyzed using Sigma Chemical Co. assay kit #366 UV in which the concentration of ATP is determined using phosphoglyceric phosphokinase and glyceraldehyde phosphate dehydrogenase and reduced coenzyme NADH. The decreased absorbance at 340 nm is indicative of coenzyme oxidation and is proportional to the concentration of ATP (adenosine 5′ triphosphate) in solution.

The concentration of $NAD^+$ can be determined using any of a number of enzymatic assay techniques in which the tested sample is introduced to an assay mixture in which an enzyme specifically reduces or oxidizes this coenzyme in the process of enzymatically oxidizing or reducing a specified substrate as in the case of glucose dehydrogenase, glyceraldehyde dehydrogenase, hydroxysteroid dehydrogenase or any of the other dehydrogenases commercially available. The increase or decrease in absorbance at 340 nm is proportional to the concentration of oxidized or reduced NAD.

Other methods of determining the concentration of these organic compounds can be accomplished using mass spectrophotometry, infrared spectrophotometry or a variety of other techniques. The analysis techniques described above are used in order to allow for quick small sample determinations during the flow through process so that flow rate and component concentrations is accomplished while the process are "in mid-stream".

In the preferred in vitro process, outlined generally in FIG. 1, an aqueous substrate solution containing concentrations of the carbohydrate monosaccharide, d-glucose, is passed successively through reaction chamber A (reactions Ia and/or Ib, II, and III), reaction chamber B (reactions IV, V, VI, and VII), reaction chamber C (reactions VIII, IX, and X) and reaction chamber D (reactions XI and XII). The effluent or "beer" from reaction chamber D contains a high percentage, e.g., up to 60%, ethanol. Carbon dioxide, a commercially valuable byproduct, is also recovered from chamber D.

The sugar solution is introduced through inlet line 21 into reaction chamber A along with the coenzyme ATP and a magnesium salt in a 1:2:2 molar ratio. The pH is adjusted to 7.0 and the temperature in reaction chamber A is maintained at 37° C.

The solution, leaving reaction chamber A through a line 23 connecting chambers A and B, contains fructose 1,6-diphosphate and ADP in association with $Mg^{++}$. The concentrations of glucose and F1,6dP are analyzed to determine whether the conditions and flow rate in reaction chamber A are optimizing product (F1,6dP) formation. The flow rate through reaction chamber A is adjusted to minimize unmodified d-glucose occuring in the solution leaving reaction chamber A.

The amount of $ADPMg^{++}$ is also determined, and, depending on its concentration, is allowed to continue through line 23 to reaction chamber B where it serves as a substrate or alternately is partially collected and directed through a line 25 to reaction chamber C where it also serves as a substrate.

The F1,6dP and ADP in line 23 are mixed with $NAD^+$ from a line 27 and, if necessary, additional $ADPMg^{2+}$ from a line 29. $K^+$, $Zn^{++}$ and $Fe^{++}$ are preferably also added to the solution entering chamber B. The concentrations of the coenzymes and cofactors entering chamber B are adjusted according to the concentration of F1,6dP entering the chamber. The pH and temperature are adjusted to 7.6 and 30° C., respectively.

The solution leaving reaction chamber B through line 31, which interconnects chambers B and C, contains high concentrations of ATP, NADH and 3 phosphoglycerate (3PG). The flow rate is adjusted to maximize 3PG production as determined by assay. The ATP produced in chamber B is extracted from the solution leaving chamber B because it inhibits reaction X in reaction chamber C, and the recovered ATP is reintroduced into reaction chamber A via lines 32, 32a, 33. Some of the ATP may also be drawn from line 32a through a line 35 and converted to ADP before distribution through line 29 into reaction chamber B or a line 37 into reaction chamber C. Preferably, the potassium, zinc and ferrous ions are recycled via line 41 into the inlet end of chamber B.

The NADH is also monitored, and, depending on its concentration, is allowed to pass through chamber C to chamber D where it serves as a substrate, or collected and directed either through lines 43, 42 to a line 46 which interconnects chambers C and D or through lines 43, 44 to a converter 45 in which NADH is oxidized to $NAD^+$ for reentry through line 27 into reaction chamber B.

The 3PG entering reaction chamber C through line 31 is mixed with ADP from line 37. In addition, metal ions $Mg^{++}$, $Mn^{++}$, $K^+$, $Rb^+$ and $Cs^+$ are added to maximize reaction rates within chamber C. Fluoride (if present) is extracted to optimize the enolase catalyzed reaction (reaction IX). $Co^{++}$, if present, is extracted to optimize the pyruvate kinase catalyzed reaction (reaction X). The pH and temperature are adjusted to 7.0 and 24° C., respectively, and the solution is pumped into reaction chamber C at a rate which optimizes pyruvate production as determined by monitoring pyruvate in the effluent of chamber C.

The effluent leaving chamber C through line 45 contains ATP which is extracted and directed through lines 49, 32a, 35 to the converter 36 where it is converted to ADP for recycling through chambers B or C. The metal ions are preferably recycled back to reaction chamber C through a line 51. Chamber C effluent is also monitored for NADH which has passed unchanged through the chamber and if in proper concentration, is allowed to pass along with the pyruvate into reaction chamber D through line 45. Otherwise, it is partially collected and diverted through line 48 to converter 46 where it is oxidized to NAD+.

The solution containing NADH and pyruvate is adjusted to pH 6.0 and 25° C. prior to admission into reaction chamber D. Chamber D is connected to a continuous vacuum to remove $CO_2$ produced in reaction XI. The oxidized coenzyme NAD+ and end product ethanol exit chamber D through line 55. The ethanol flows through line 57 to distillation apparatus 59. The NAD+ is collected and distributed through lines 62, 63, 27 to Chamber B or through lines 62, 64 to a converter 69 which reduces the NAD+ to NADH for recycling through line 68 Chamber D. $CO_2$ is drawn from chamber D by a vaccum pump 71 and directed through line 72 to storage vessel 73.

Figure 2:
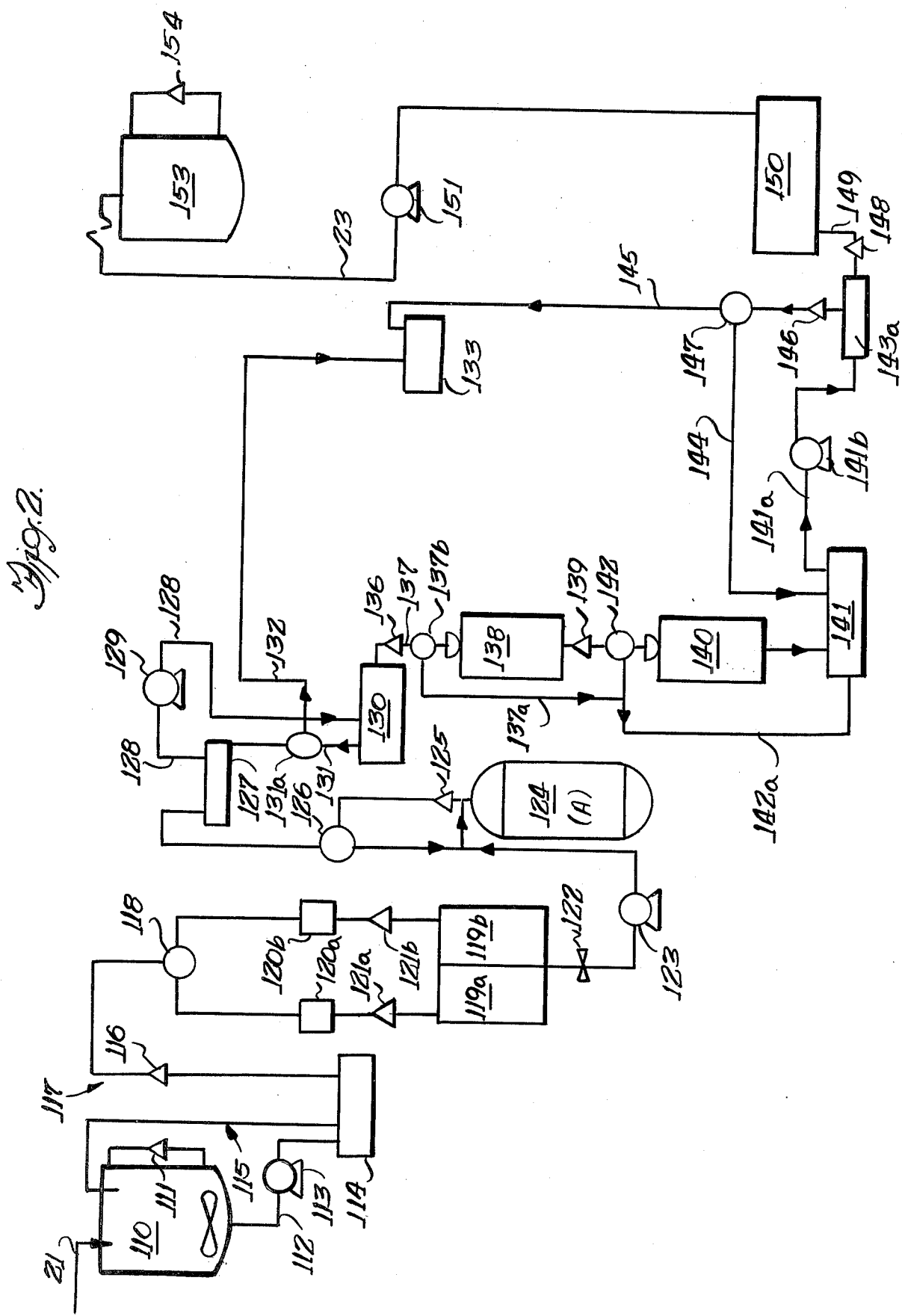
FIG. 2 is a more detailed schematic of a portion of the system of FIG. 1 showing in greater detail one of the reaction chambers and its associated apparatus.

Referring now to FIG. 2, the functioning of reaction chamber A and its associated apparatus is described in greater detail.

The aqueous solution containing initial substrate material (d-glucose) is admitted to a substrate suspension tank 110, and brought to the appropriate concentration in deionized water as determined by an Auto-Continuous-Flow-Analysis-Station (ACFAS) 111. Suspended substrates are drawn through a line 112 by a pump 113, and particulate material is extracted by an ultrafiltration unit 114 from where the retentate suspension is returned to the suspension tank 110 through a line 115 and the filtrate directed onward through a line 117. Filtered suspended substrate, passing through line 117, is monitored by an ACFAS 116 and alternately distributed by a flow control valve 118 to final preparation tanks 119a and b. Substrate conversion optimization is accomplished by additions of co-components and salts and adjustments of pH and temperature as monitored by ACFAS's 121 a, b and controlled and provided by support systems 120. Optimized substrate is drawn through a control valve 122 alternately from tanks 119a, b by a pump 123 and delivered to the reaction chamber 124 (A). ACFAS 125 analyzes resulting end product (F1,6dP), and the flow is directed by a valve 126 either back through reaction chamber 124 (A) or into a reservoir 127. End product solution is drawn from the reservoir 127 by a pump 129 through a line 128 and an ultrafiltration unit 130. Unfiltered retentate material is either returned to the reservoir 127 through a line 131 or directed by control valve 131a through a line 132 to a reservoir 133 for holding or examination. Filtered solution, monitored for end product and coenzyme concentration by ACFAS 136, passes through a line 137 to control valve 137b which directs the solution to a co-component/coenzyme extraction system 138, if necessary; alternately it is passed through line 137a to holding reservior 141. If the solution is directed thru extraction system 138, it is monitored again by an ACFAS 139 and alternatively directed by a valve 142 through a second co-component/coenzyme extraction system 140 into a holding reservoir 141 or directly into the holding reservoir thru line 142a, 137a. Material from the reservoir is drawn through a line 141a by a pump 141b to an ultrafiltration unit 143. Unfiltered retentate material is either returned to reservoir 141 through a line 144 or passed through a line 145 to the holding and examining reservoir 133 as controlled by an ACFAS 146 and a valve 147. Filtered material is monitored for end product concentration by ACFAS 148 and drawn through a line 149 to a reservoir 150. A pump 151 moves end product held in reservoir 150 through line 23 to a primary substrate reservoir 153 of chamber B at a rate controlled by an ACFAS 154.

The remaining chambers B, C and D have similar associated apparatus and will not be described herein in greater detail. Modifications which would be apparent to one with ordinary skill in the art are made as required by the use of different cofactors, coenzymes and substrate.

The removal of coenzymes such as ATP, ADP, NAD+ and NADH in the extraction systems, indicated generally at 138, for recycling and necessary regeneration is preferably achieved through means of affinity binding material. Coenzymes ATP/ADP and NAD+/NADH are extracted from solution as described generally in reference to FIGS. 3-6. Coenzyme affinity binding material can be of several types: covalently bound-protein having a strong affinity for a specific coenzyme; bound Poly U (Polyuridine is an organic molecule which has a strong affinity for hydrogen bonding with the adenine bases in ATP/ADP/NAD+/NADH); ionic exchange; and commercial matricies such as AFFI 501, and 601 produced by Bio Rad Chemical Co. This matrix material generally associates with and holds molecules (coenzymes) to be extracted (adsorbed) through noncovalent bonding (i.e., ionic, hydrophobic, Van Der Waal's and hydrogen bonding).

The affinity material is contained in loaded affinity chambers 200 which are inserted in-line for removal of a particular coenzyme and removed when saturated for regeneration of affinity material and recovery of the adsorbed coenzyme. The chambers 200 which are loaded with affinity matrix material are sealed with air lock caps 202 and mounted into magazines 204 (FIG. 3) for storage at 0°–4° C. The number of affinity chambers contained in a magazine, and thus the amount of binding material, is calculated to accommodate an anticipated adsorption requirement based on a fixed rate of flow over a period of time.

A single affinity chamber 200 is moved into position, and the air tight seals 202 are perforated by connecting members 206, 208 to insert the chamber in-line. Bindable material is retained within the chamber, and the solution leaving the chamber is monitored for chamber saturation or malfunction by analyzing the absorbance across the infrared, visual and ultraviolet spectrum in a flow-through analysis chamber 210. Chamber saturation is determined by reflecting the analysis results against preestablished spectral standards. Variations from mirror image reflection with standards initiates automatic flow shut-off, chamber separation and chamber reload from the magazine 204.

Affinity matrix material is purged from saturated chambers 200 and spread onto a thin layer porous bed 214 in the upper chamber 216 of desorption system (FIG. 5) with a pore size substantially smaller than the matrix material. An appropriate buffer is sprayed onto the bed 214 and allowed to seep through or is pulled through the porous bed under vacuum into the lower chamber 216a to wash the unbound material away from the affinity matrix. The wash solution is collected, and the buffer wash is repeated again to fill the upper and lower chambers while an electric current is passed through the solution in both chambers desorbing the bound material and isolating it in the lower chamber. The mechanism for electrophoretic desorption is simple. Co-enzymes or other molecules which are extracted are noncovalently bound to affinity material and thus exist in bound and unbound states of equilibrium.

Once unbound material is washed away in the initial buffer wash, some initially bound material (co-enzyme molecules) will dissociate to re-establish the equilibrium. When an electric field is applied, the free material will electrophorese away causing the remaining bound material to continue dissociation. Therefore, a trail of unbound co-enzyme molecules will follow the initially desorbed material as it migrates through the porous bed into the lower chamber of the desorption system. The desorption rate can be maximized to discourage readsorption of the free co-enzyme to matrix particles by spreading the matrix material over a larger surface area. The electric field is applied in a uniform manner over the entire bed dimension. The upper and lower buffers provide continuity for the current flow between the electrodes. Current direction and amperage requirements are determined by the matrix material and coenzymes involved. The desorbed coenzyme passes through the porous bed leaving the desorbed matrix material for preparation and reloading into affinity chambers. This desorption system is automated to interface with a continuous flow ethanol production process. Affinity matrix analysis specifications and adsorbtion criteria can be altered to accommodate the requirements of each enzyme reaction chamber.

As seen in FIG. 6, the solution leaving the desorption lower chamber 216a through line 217 is driven by a pump 218 through a control valve 220 to one of three possible locations. Initial washes contain both unbound coenzyme and an unbound quantity of intermediate carbohydrate and other components. These washes are returned via a line 222 to the line 137, FIG. 2 for further processing. Desorption washes containing coenzymes not needing modification flow from the control valve 220 through a line 224 to a coenzyme concentration chamber 226 wherein the suspended coenzyme concentration is standardized by evaporation, dilution, lyophilization, ultrafiltration etc. The concentrated coenzyme solution is driven by a pump 228 to a storage preparation chamber 230 where the specific coenzyme solution is prepared for entry into the in vitro final preparation tanks 119a,b (FIG. 2) by adjusting pH and temperature. This solution is either stored at 4° C. or less or immediately used in the reaction chamber A, B, C or D.

Desorption washes containing coenzymes which require modification pass through a line 240 to a system specific to the modification of each coenzyme isolated. This system involves a concentration standardization unit 242, a pre-modification chamber 241, a coenzyme modifying reaction chamber 246 and a storage utilization preparation chamber 248. End products from these biomodification systems are returned to the final preparation tanks 19a,b.

The above-described system produces an aqueous ethanol solution or "beer" containing as much as about 60% by weight ethanol. The ethanol can be concentrated employing any of the known and conventional techniques and is advantageously concentrated by an anhydrous distillation process.

Despite the somewhat complex nature of the apparatus required to continuously monitor and adjust the system, and despite the requirement of expensive enzymes and cofactors, ethanol may be produced by the system more cheaply than by conventional fermentation processes. Immobilization of the enzymes substantially reduces the cost of enzymes for the system by taking advantage of their continuous catalytic abilities. Recovery and recycling of relatively expensive coenzymes such as ATP/ADP and NAD+/NADH represents a further important efficiency achieved by the system of the present invention. The various reactions of the fermentation process are grouped in vitro in a manner which maximizes product formation in each group. Far less energy is required to concentrate the ethanol from highly concentrated "beer" than is required to concentrate ethanol from the weakly concentrated "beer" produced by conventional fermentation techniques. Furthermore, the "beer" contains no cell culture material which must be disposed of.

While the system, as herein described, produces ethanol more cheaply than conventional fermentation techniques, it is contemplated that refinements in the process may result in additional efficiencies. For example, it is contemplated that genetic engineering techniques will not only lessen the cost of enzymes but are capable of producing enzymes with optimal reaction temperatures well above those of currently available enzymes. Enzymes are contemplated which will maintain their catalytic activity at temperatures in excess of 80° C. making it possible to realize the potential of the greater reaction rates which normally occur at higher temperatures as well as direct distillation. The affinity material desorption process might be simplified by binding the affinity material directly to a ridged porous matrix structure which serves as a desorption bed. Such a system might be purged in a continuous flow system.

While the invention has been described in terms of a preferred embodiment, modifications obvious to one with ordinary skill in the art may be made without departing from the scope of the invention. For example, it is known that certain glycolytic intermediates may be produced by alternate enzymatic routes, e.g., the pentose shunt pathway and Entner-Doudoroff pathway, and enzymatic fermentation along such pathways are considered within the scope of the invention.

Various features of the invention are set forth in the following claims.

What is claimed is

1. A method of producing ethanol comprising
    providing a first reaction zone containing an enzymatic protein selected from the group consisting of hexokinase and glucokinase plus the enzymatic proteins phosphoglucose isomerase and phosphofructokinase,
    providing a second reaction zone containing the enzymatic proteins aldose, triose phosphate isomerase, glyceraldehyde-3-phosphate dehydrogenase, and phosphoglycerate kinase,
    providing a third reaction zone containing the enzymatic proteins phosphoglyceromutase, enolase and pyruvate kinase,
    providing a fourth reaction zone containing the enzymatic proteins pyruvate decarboxylase and alcohol dehydrogenase,
    retaining said enzymatic proteins in their respective reaction zones,
    passing a fermentable sugar solution successively through said reaction zones,
    adding coenzymes and cofactors to said reaction zones as required for the enzymatic proteins in each zone to perform their catalytic functions, and
    recovering ethanol from the fourth reaction zone.

2. A method according to claim 1 which is carried out as a continuous process including the steps of recovering coenzymes exiting certain of said reactions zones and reintroducing said recovered coenzymes into appropriate reactions zones.

3. A method according to claim 2 including the steps of modifying some of said recovered coenzyme prior to reintroduction thereof.

4. A method according to claim 1 wherein said enzymatic proteins are retained in said reactions zones by immobilization.

5. A method according to claim 1 wherein said enzymatic proteins are retained in said reactions zone by molecular filters.

6. A method of producing ethanol comprising
immobilizing the enzymatic proteins whose combined catalytic activity completes the reaction sequence of the glycolytic pathway for the conversion of fermentable sugars to ethanol,
disposing said immobilized enzymatic proteins in four segregated reaction chambers arranged in accordance with the reaction sequence of the glycolytic pathway,
adding coenzymes and cofactors to a fermentable sugar substrate solution,
introducing said sugar substrate solution plus said additives into said first chamber containing an enzymatic protein selected from the group consisting of hexokinase and glucokinase, plus the enzymatic proteins phosphoglucose isomerase and phosphofructokinase,
introducing the solution exiting from said first chamber into said second chamber containing the enzymatic proteins aldolase, triose phosphate isomerase, glyceraldehyde-3-phosphate dehydrogenase and phosphoglycerate kinase,
introducing the solution exiting from said second chamber into said third chamber containing the enzymatic proteins phosphoglyceromutase, enolase and pyruvate kinase,
introducing the solution exiting from said third chamber into said fourth chamber containing the enzymatic proteins pyruvate decarboxylase and alcohol dehydrogenase, and
recovering ethanol from said fourth chamber.

7. A method according to claim 6 which is carried out as a continuous process including the steps of introducing NAD+ into said second chamber, recovering NAD+ from said solution exiting from said fourth chamber and returning said recovered NAD+ to said second chamber.

8. A method according to claim 6 including the steps of introducing ATP into said first chamber, intoducing ADP into said second chamber and into said third chamber and recovering ATP from said third chamber.

9. A method according to claim 8 including recovering ATP from said second chamber.

10. A method according to claim 6 including the steps of continuously monitoring said solution exiting from each of said chambers,
adding cofactors and coenzymes required for the reactions in each of said chambers, and
adjusting the rates of introduction of said substrate, said cofactors and said coenzymes into said respective chambers in response to said monitoring to generally maximize product formation in each of said chambers.

11. A system for enzymatically convering sugar to ethanol comprising
four successive reaction chambers containing enzymatic proteins arranged in sequence for conversion of sugar to ethanol and $CO_2$ by the glycolytic pathway,
said first chamber containing an enzymatic protein selected from the group consisting of hexokinase and glucokinase, plus the enzymatic proteins phosphoglucose isomerase and phosphofructokinase,
said second chamber containing the enzymatic proteins aldolase, triose phosphate isomerase, glyceraldehyde-3-phosphate dehydrogenase and phosphoglycerate kinase,
said third chamber containing the enzymatic proteins phosphoglyceromutase, enolase, pyruvate kinase,
said fourth chamber containing the enzymatic proteins pyruvate decarboxylase and alcohol dehydrogenase,
means for retaining said enzymatic proteins in each of said chambers,
means for causing a fermentable sugar substrate solution to flow sequentially through said reaction chambers so as to come in contact with said enzymatic proteins,
means for introducing necessary coenzymes and cofactors to said reaction chambers along with said flowing sugar substrate solution, and
means for recovering ethanol from said fourth reaction chamber.

12. A method of producing ethanol comprising
immobilizing the enzymatic proteins whose combined catalytic activity completes the reaction sequence of the glycolytic pathway for the conversions of fermentable sugars to ethanol, said enzymes including an enzymatic protein selected from the group consisting of hexokinase and glucokinase, plus the enzymatic proteins phosphoglucose isomerase, phosphofructokinase, aldolase, triose phosphate isomerase, glyceraldehyde-3-phosphate dehydrogenase, phosphoglycerate kinase, phosphoglyceromutase, enolase, pyruvate kinase, pyruvate decarboxylase, and alcohol dehydrogenase,
grouping said immobilized enzymatic proteins in sequenced reaction zones, the enzymatic proteins phosphoglucose isomerase and phosphofructokinase being grouped together in one reaction zone, said enzymatic proteins aldolase, triose phosphate isomerase, glyceraldehyde-3-phosphate dehydrogenase, and phosphoglycerate kinase being grouped together in another reaction zone and said enzymatic proteins phosphoglyceromutase, enolase and pyruvate kinase being grouped in yet another reaction zone,
adding coenzymes and cofactors to a fermentable sugar substrate solution,
flowing said sugar substrate solution plus said additives to said sequenced reaction zones containing said immobilized enzymatic proteins, and
recovering ethanol from the last zone.

13. A method according to claim 12 including the steps of continuously monitoring said solution exiting from each of said reaction zones,
adding cofactors and coenzymes required for the reactions in each of said reaction zones, and
adjusting the rates of introduction of said substrate, said cofactors and said coenzymes into said respective reaction zones in response to said monitoring to generally maximize product formation in each of said reaction zones.

14. A method of producing ethanol comprising

Providing a sequenced series of reaction zones containing in total the enzymatic proteins which catalyze the steps the glycolytic pathway that converts a fermentable sugar into ethanol, the enzymatic proteins including in sequence an enzymatic protein selected from the group consisting of hexokinase and glucokinase, plus the enzymatic proteins phosphoglucose isomerase, phosphofructokinase, aldolase, triose phosphate isomerase, glyceraldehyde-3-phosphate dehydrogenase, phosphoglycerate kinase, phosphoglyceromutase, enolase, pyruvate kinase, pyruvate decarboxylase, and alcohol dehydrogenase, said enzymatic proteins phosphyglucose isomerase and phosphofructokinase being grouped together in one reaction zone, said enzymatic proteins aldolase, triose phosphate isomerase, glyceraldehyde-3-phosphate dehydrogenase and phosphoglycerate kinase being grouped together in another reaction zone and said enzymatic proteins phosphoglyceromutase, enolase and pyruvate kinase being grouped together in yet another reaction zone, retaining said enzymatic proteins in their respective reaction zones, passing a fermentable sugar solution successively through said reaction zones, adding coenzymes and cofactors to said reaction zones as required for the enzymatic proteins in each reaction zone to perform their catalytic function, and recovering ethanol from the last reaction zone.

15. A method according to claim 14 which is carried out as a continous process including the steps of recovering coenzymes exiting certain of said reaction zones and reintroducing said recovered coenzymes to appropriate reaction zones.

16. A method according to claim 14 including the steps of modifying said recovered coenzymes prior to reintroduction thereof.

17. A method according to claim 14 wherein said enzymatic proteins are retained in said reaction zones by molecular filters.

18. A system for enzymatically converting sugar to ethanol comprising a plurality of reaction chambers containing enzymatic proteins arranged in sequence for conversion of sugar to ethanol by the glycolytic pathway, said reaction chambers in total containing an enzymatic protein selected from the group consisting of hexokinase and glucokinase, plus the enzymatic proteins phosphoglucose isomerase, phosphofructokinase, aldolase, triose phosphate isomerase, glyceraldehyde-3-phosphate dehydrogenase, phosphoglycerate kinase, phosphoglyceromutase, enolase, pyruvate kinase, pyruvate decarboxylase and alcohol dehydrogenase, means for retaining said enzymatic proteins in each of said chambers, the enzymatic proteins phosphoglucose isomerase and phosphofructokinase being grouped together in one chamber, the enzymatic proteins aldolase, triose phophate isomerase, glyceraldehyde-3-phosphate dehydrogenase and phosphoglycerate kinase being grouped together in another chamber and said enzymatic proteins phosphoglyceromutase, enolase and pyruvate kinase being grouped together in another chamber.

* * * * *